US012685685B2

(12) United States Patent
Kogawa et al.

(10) Patent No.: US 12,685,685 B2
(45) Date of Patent: Jul. 21, 2026

(54) EXCRETION CARE ASSISTANCE DEVICE AND EXCRETION CARE ASSISTANCE METHOD

(71) Applicant: SINTOKOGIO, LTD., Nagoya (JP)

(72) Inventors: Akifumi Kogawa, Nagoya (JP);
Masataka Shiraki, Nagoya (JP);
Masahiko Nagasaka, Nagoya (JP)

(73) Assignee: SINTOKOGIO, LTD., Aichi (JP)

( * ) Notice: Subject to any disclaimer, the term of this patent is extended or adjusted under 35 U.S.C. 154(b) by 327 days.

(21) Appl. No.: 18/537,322

(22) Filed: Dec. 12, 2023

(65) Prior Publication Data

US 2024/0261163 A1 Aug. 8, 2024

(30) Foreign Application Priority Data

Feb. 8, 2023 (JP) ................................. 2023-017845

(51) Int. Cl.
| | |
|---|---|
| *A61G 9/00* | (2006.01) |
| *A61G 9/02* | (2006.01) |
| *G16H 10/60* | (2018.01) |
| *G16H 40/20* | (2018.01) |
| *A61F 13/42* | (2006.01) |

(52) U.S. Cl.
CPC .................. *A61G 9/00* (2013.01); *A61G 9/02* (2013.01); *G16H 10/60* (2018.01); *G16H 40/20* (2018.01); *A61F 13/42* (2013.01)

(58) Field of Classification Search
CPC .... A61G 9/00; A61G 9/02; A61B 5/00; A61B 5/20; A61F 13/42; A61F 13/49; G16H 10/60; G16H 20/00; G16H 40/20; G06F 21/31; G06F 21/44; G06F 21/629
See application file for complete search history.

(56) References Cited

U.S. PATENT DOCUMENTS

| | | | | |
|---|---|---|---|---|
| 2021/0151177 A1* | 5/2021 | Ohashi | ................... | G16H 40/67 |
| 2022/0233363 A1* | 7/2022 | Heirman | ................. | A61F 13/49 |
| 2024/0265086 A1* | 8/2024 | Ishikawa | ............... | G06F 21/629 |
| 2024/0350056 A1* | 10/2024 | Laing | .................... | A61B 5/208 |

FOREIGN PATENT DOCUMENTS

JP 2014-33745 A 2/2014

\* cited by examiner

*Primary Examiner* — Van T Trieu
(74) *Attorney, Agent, or Firm* — Harness, Dickey & Pierce, P.L.C.

(57) ABSTRACT

An excretion care assistance device includes a processor. The processor is configured to carry out a first specification process of specifying defecation times of care-receivers on the basis of sensor terminals and a second specification process of specifying a time at which group excretion care is to be started for at least one care-receiver group, in accordance with a frequency distribution indicative of a total number of times of defecation in each of a plurality of time periods, the frequency distribution being determined from the defecation times that have been specified in the first specification process.

7 Claims, 5 Drawing Sheets

M2

EXCRETION CARE ASSISTANCE DEVICE AND EXCRETION CARE ASSISTANCE METHOD

This Nonprovisional application claims priority under 35 U.S.C. § 119 on Patent Application No. 2023-017845 filed in Japan on Feb. 8, 2023, the entire contents of which are hereby incorporated by reference.

TECHNICAL FIELD

The present invention relates to an excretion care assistance device and an excretion care assistance method each for assisting a caregiver in providing excretion care for care-receivers in a medical/nursing facility or the like.

BACKGROUND ART

Excretion care provided in a medical/nursing facility or the like includes group excretion care and individual excretion care. The group excretion care refers to excretion care provided for a group of care-receivers included in a care-receiver group several times a day at predetermined times. The individual excretion care refers to excretion care provided only for each care-receiver who needs excretion care. In many facilities, the group excretion care is provided every day at fixed times, and the individual excretion care is provided in a case where the group excretion care cannot handle (for example, a case where a care-receiver excretes after the group excretion care has been provided).

In the group excretion care, the excretion care is provided irrespective of whether or not the care-receiver has excreted, and thus a miss, in which the excretion care is provided even for who has not excreted, sometimes occurs. This results in waste of diapers and waste of effort of the caregiver. In addition, a large number of times of the misses in the group excretion care leads to an increase of the number of times of individual excretion care. This puts a great burden on the caregiver.

For example, a technique disclosed in Patent Literature 1 is known as a technique for reducing the burden of excretion care on the caregiver. The technique disclosed in Patent Literature 1 determines, on the basis of an output signal from an odor sensor and an output signal from a humidity sensor, the type of excreta of a care-receiver and whether the leakage from a diaper of the care receiver has occurred, and then notifies a caregiver of the degree of urgency of excretion care.

CITATION LIST

Patent Literature

Patent Literature 1

Japanese Patent Application Publication Tokukai No. 2014-33745

SUMMARY OF INVENTION

Technical Problem

The technique as described above makes notification of the urgency of excretion care so as to enable efficient individual excretion care. This, however, does not reduce the number of times of the excretion care itself and thus does not contribute to a substantial reduction in burden of the excretion care on the caregiver.

It is an object of an aspect of the present invention to achieve an excretion care assistance device and an excretion care assistance method, each of which makes it possible to provide group excretion care after more care-receivers have excreted, to reduce the frequency of individual excretion care, so that it is possible to reduce a burden on a caregiver.

Solution to Problem

An excretion care assistance device in accordance with an aspect of the present invention includes a processor configured to carry out a first specification process and a second specification process. Further, an excretion care assistance method in accordance with an aspect of the present invention includes a first specification process and a second specification process. Here, the first specification process is a process with the processor specifying defecation times of care-receivers included in at least one care-receiver group on the basis of output signals from sensor terminals which are worn by the care-receivers and which include excretion sensors. The second specification process is a process of specifying a time at which group excretion care is to be started for the at least one care-receiver group, in accordance with a frequency distribution indicative of a total number of times of defecation in each of a plurality of time periods, the frequency distribution being determined from the defecation times that have been specified in the first specification process.

Advantageous Effects of Invention

It is possible to achieve an excretion care assistance device and an excretion care assistance method, each of which makes it possible to provide group excretion care after more care-receivers have excreted, to reduce the frequency of individual excretion care, so that it is possible to reduce a burden on a caregiver.

DESCRIPTION OF EMBODIMENTS

With reference to FIGS. 1 to 6, the following description will discuss an embodiment of the present invention. Note that, in the present specification, the phrase "excretion care" typically refers to excretion care provided when a care-receiver Ua has defecated (for example, exchange of diapers and cleaning of an anus and the area thereberground), and the "group excretion care" and the "individual excretion care" are also collectively referred to as "excretion care". Further, the "care-receiver group" is a set of care-receivers Ua. There are n care-receiver group(s) (n is any natural number of not less than 1) in a facility that uses an excretion care assistance system S (hereinafter, also referred to simply as "facility"). The number and a combination of care-receivers Ua included in each of the n care-receiver groups can be set as appropriate. For example, the care-receiver group may include a plurality of care-receivers Ua who live on the same floor in the facility and may include a combination of care-receivers Ua which is made on the basis of nursing care levels or symptoms.

(Configuration of Excretion Care Assistance System)

Figure 1:
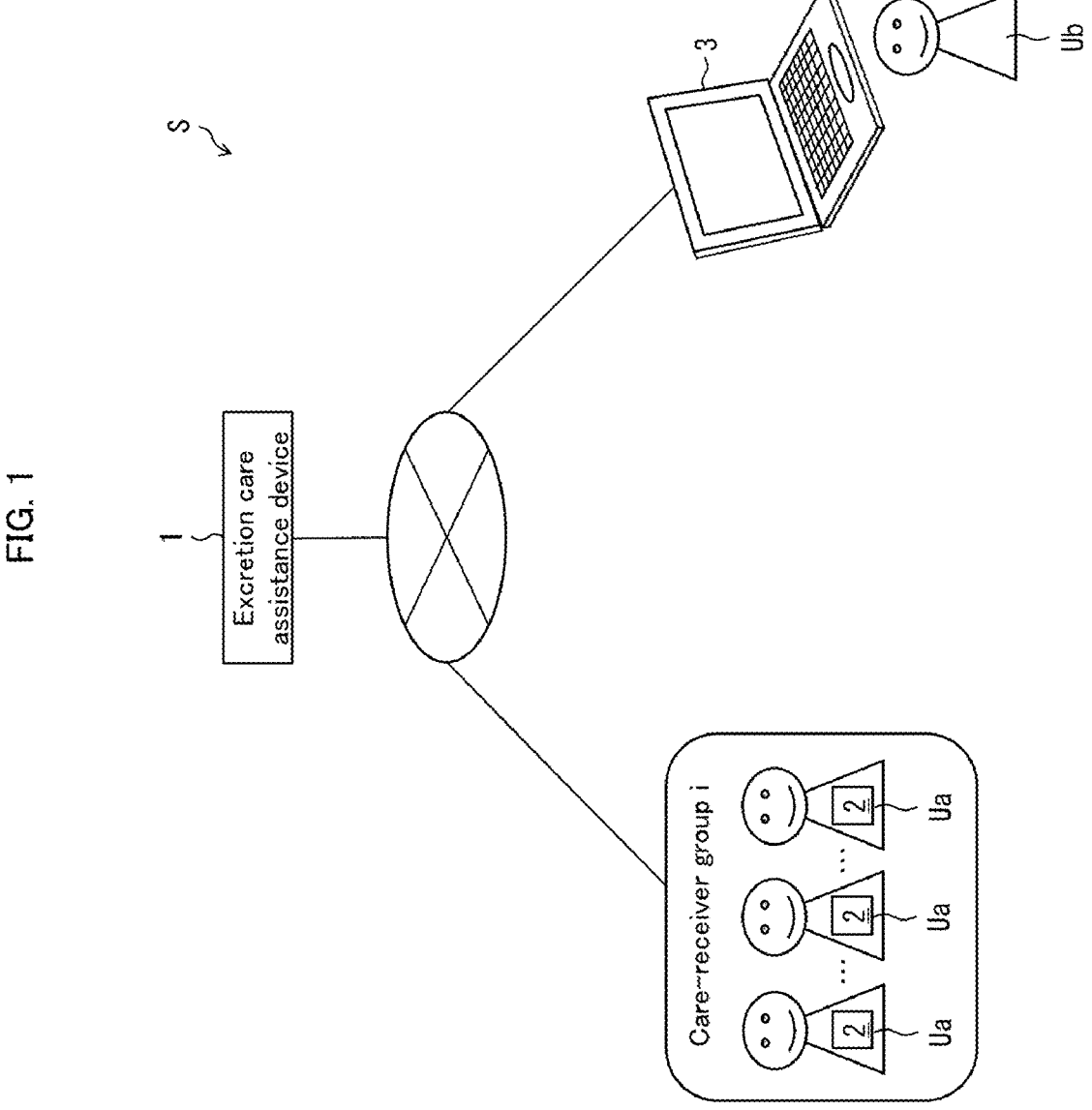
FIG. 1 is a view schematically illustrating a configuration of an excretion care assistance system in accordance with Embodiment 1 and Embodiment 2.

With reference to FIG. 1, a configuration of the excretion care assistance system S will be described. FIG. 1 is a view to schematically illustrating a configuration of the excretion care assistance system S.

The excretion care assistance system S is a system for assisting a caregiver Ub in providing excretion care in a facility, the purpose of which is to provide care services or medical services.

As illustrated in FIG. 1, the excretion care assistance system S includes an excretion care assistance device 1, a plurality of sensor terminals 2, and at least one notification terminal 3. The sensor terminals 2 and the notification terminal 3 are communicable with the excretion care assistance device 1 via a network.

The sensor terminals 2 are provided to the respective care-receivers Ua included in a care-receiver group i (i is a natural number of not less than 1 and not more than n). For example, the sensor terminals 2 are provided inside undergarments (such as diapers or underwear) of the care-receivers Ua. The sensor terminal 2 contains an excretion sensor therein. In a case where the excretion sensor of the sensor terminal 2 detects defecation of the care-receiver Ua, the sensor terminal 2 transmits an output signal indicative of the detection of the defecation (hereinafter, also referred to as "defecation detection signal") to the excretion care assistance device 1.

On reception of the defecation detection signals from the sensor terminals 2, the excretion care assistance device 1 specifies, on the basis of the defecation detection signals received, defecation times at which the care-receivers Ua defecated. Further, the excretion care assistance device 1 generates, from the defecation times specified, a frequency distribution indicative of the total number of times of defecation in each of a plurality of time periods. On the basis of the frequency distribution generated, the excretion care assistance device 1 specifies a time at which group excretion care is to be started for the care-receiver group i, and/or estimates the number of the caregivers Ub needed for excretion care to be provided for the care-receiver group i. Furthermore, the excretion care assistance device 1 transmits, to the notification terminal 3, information including the specified time at which the group excretion care is to be started (hereinafter, also referred to as "first notification information") and/or information including a result of estimation of the number of the caregivers Ub needed for the excretion care (hereinafter, also referred to as "second notification information"). The present embodiment assumes that the excretion care assistance device 1 is a workstation disposed outside the facility that uses the excretion care assistance system S (for example, disposed in a data center). However, the present invention is not limited to this. The excretion care assistance device 1 can be, for example, a desktop personal computer (PC) disposed in the facility that uses the excretion care assistance system S.

The notification terminal 3 is a terminal containing a display therein and displays, on the display, various pieces of information received from the excretion care assistance device 1. On reception of the first notification information from the excretion care assistance device 1, the notification terminal 3 displays, on the display, a screen indicative of a list of times at which the excretion care is to be started. On reception of the second notification information from the excretion care assistance device 1, the notification terminal 3 displays, on the display, a screen indicative of a list of the numbers of the caregivers Ub needed for the excretion care. The notification terminal 3 may transmit a transmission request for the first notification information and/or a transmission request for the second notification information, to the excretion care assistance device 1. The present embodiment assumes that the notification terminal 3 is a laptop PC disposed in the facility that uses the excretion care assistance system S (for example, a station in which the caregivers Ub are present). However, the present invention is not limited to this. The notification terminal 3 can be, for example, a desktop PC, a tablet PC, a smartphone, or the like. Alternatively, these devices each of which is usable as the notification terminal 3 can coexist in the excretion care assistance system S.

(Configuration of Excretion Care Assistance Device)

Figure 2:
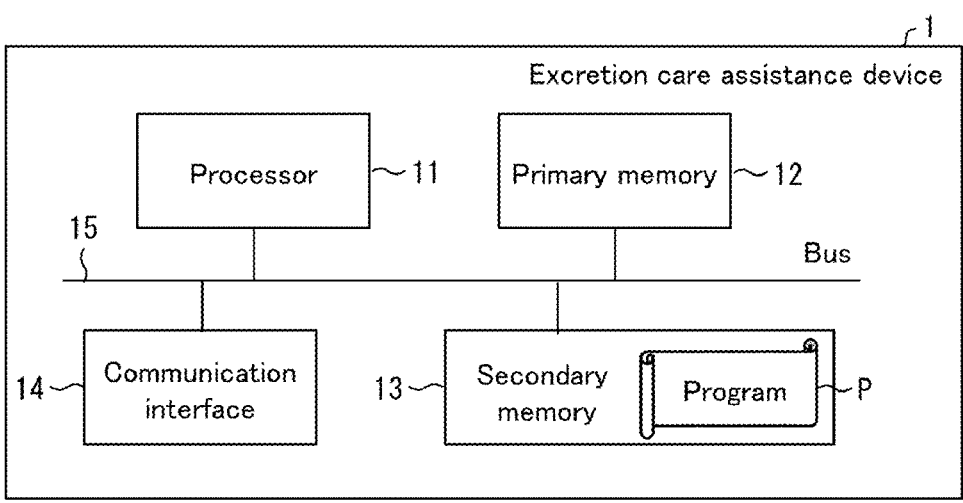
FIG. 2 is a block diagram illustrating a configuration of excretion care assistance device included in the excretion care assistance system illustrated in FIG. 1.

With reference to FIG. 2, a configuration of the excretion care assistance device 1 will be described. FIG. 2 is a block diagram illustrating the configuration of the excretion care assistance device 1.

As illustrated in FIG. 2, the excretion care assistance device 1 includes a processor 11, a primary memory 12, a secondary memory 13, a communication interface 14, and a bus 15. The processor 11, the primary memory 12, the secondary memory 13, and the communication interface 14 are connected with each other via the bus 15. Examples of a device usable as the excretion care assistance device 1 include a workstation constituting a cloud server.

The secondary memory 13 stores an excretion care assistance program P. The processor 11 loads, on the primary memory 12, the excretion care assistance program P stored in the secondary memory 13. The processor 11 carries out processes included in an excretion care assistance method M1 or M2 (described later) in accordance with instructions included in the excretion care assistance program P loaded on the primary memory 12. Examples of a device usable as the processor 11 include a central processing unit (CPU). Examples of a device usable as the primary memory 12 include a semiconductor random access memory (RAM). Examples of a device usable as the secondary memory 13 include a hard disk drive (HDD).

The communication interface 14 is an interface for communicating with the sensor terminals 2 and the notification terminal 3 via a network. Examples of a device usable as the communication interface 14 include an Ethernet (registered trademark) interface. Examples of a usable network include a personal area network (PAN), a local area network (LAN), a campus area network (CAN), a metropolitan area network (MAN), a wide area network (WAN), a global area network (GAN), and an internetwork containing a combination thereof. The internetwork may be an intranet, or may be an extranet, or may be the Internet.

Note that the excretion care assistance program P for causing the processor 11 to provide the excretion care assistance method M1 or M2 may be stored in a computer-readable non-transitory tangible storage medium. This storage medium can be the secondary memory 13 or another storage medium. For example, a tape, a disk, a card, a semiconductor memory, a programmable logic circuit, or the like can be used as said another storage medium.

The present embodiment employs a configuration in which a single processor (processor 11) is used to carry out the excretion care assistance method M1 or M2. However, the present invention is not limited to this configuration. That is, it is alternatively possible to employ a configuration in which a plurality of processors are used to carry out the excretion care assistance method M1 or M2. In such a case, the plurality of processors for carrying out the excretion care assistance method M1 or M2 can be provided in a single computer and be communicable with each other via a bus or can be dispersedly provided in a plurality of computers and be communicable with each other via a network. For example, an alternative aspect is also possible in which processors included in the respective computers constituting a cloud server work together to carry out the excretion care assistance method M1 or M2.

(Flow of Excretion Care Assistance Method)

Figure 3:
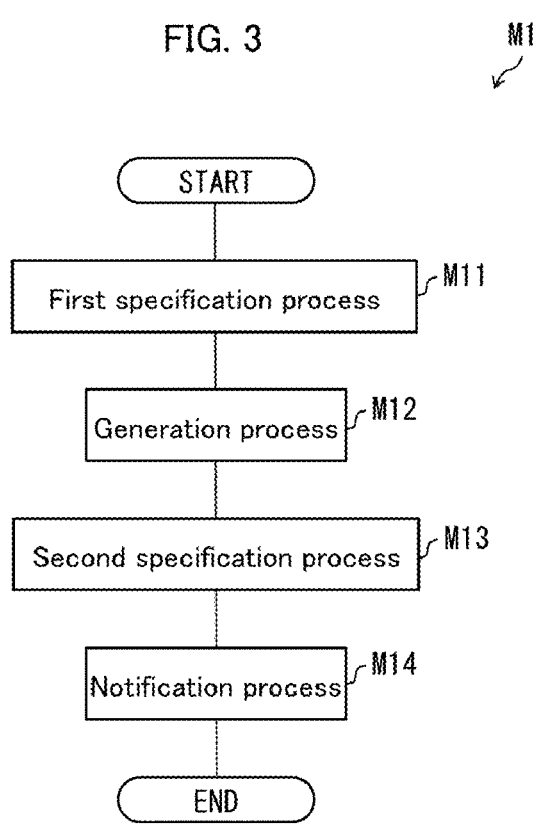
FIG. 3 is a flowchart showing a flow of an excretion care assistance method carried out in an excretion care assistance system in accordance with Embodiment 1.

With reference to FIG. 3, the excretion care assistance method M1 carried out by the excretion care assistance device 1 will be described. FIG. 3 is a flowchart illustrating a flow of the excretion care assistance method M1.

As illustrated in FIG. 3, the excretion care assistance method M1 includes a first specification process M11, a generation process M12, a second specification process M13, and a notification process M14. The timing at which the excretion care assistance device 1 carries out these processes can be set as appropriate. For example, the excretion care assistance device 1 may carry out the processes illustrated in FIG. 3 at predetermined time intervals (for example, every 24 hours) or may carry out the processes every time the excretion care assistance device 1 receives a transmission request for the first notification information from the notification terminal 3.

The first specification process M11 is a process for specifying the defecation times of the care-receivers Ua included in the care-receiver group i. In the first specification process M11, the processor 11 of the excretion care assistance device 1 specifies the defecation times of the care-receivers Ua on the basis of the defecation detection signals that the processor 11 has received from the sensor terminals 2. As the defecation time of a care-receiver Ua wearing a sensor terminal 2, the excretion care assistance device 1 specifies, for example, a time at which the excretion care assistance device 1 received a defecation detection signal from the sensor terminal 2.

Note that, the defecation times of the care-receivers Ua specified in the first specification process M11 are preferably specified in association with pieces of identification information of the care-receivers Ua corresponding to the sensor terminals 2. This enables the present embodiment to be used for other applications, such as use in nursing care reports individually for the care-receivers Ua.

The generation process M12 is a process for generating a frequency distribution indicative of the total number of times of defecation in each of the plurality of time periods, in the care-receiver group i. In the generation process M12, on the basis of the defecation times of the care-receivers Ua which have been specified in the first specification process M11, the processor 11 of the excretion care assistance device

1 generates a frequency distribution in which: classes are time periods into which one day is divided; and frequencies are the total numbers of times of defecation. Note that a time width (class width) in each of the time periods can be set as appropriate. In the present embodiment, the time width (class width) is set to 15 minutes, and the classes are set to be time periods into which one day is divided at 15-minute intervals.

The second specification process M13 is a process for specifying each time at which the group excretion care is to be started for the care-receiver group i. In the second specification process M13, the processor 11 of the excretion care assistance device 1 specifies times T1 to Tj (j is any natural number of not less than 2) at which the group excretion care is to be started for the care-receiver group i, in accordance with the frequency distribution that has been generated in the generation process M12.

Note that the number of times at which the group excretion care is to be started and which are specified in the second specification process M13 can be set as appropriate. For example, in a facility in which the group excretion care is provided four times a day, times T1 to T4 at which the group excretion care is to be started are specified. Further, respective time periods that include the times T1 to T4 can be set as appropriate.

For example, a case is assumed where, in a facility in which the group excretion care is provided four times a day, the group excretion care is provided once in each of the following time periods: a time period $\Delta T1$ from a breakfast to a lunch; a time period $\Delta T2$ from the lunch to a dinner; a time period $\Delta T3$ from the dinner to a bedtime; and a time period $\Delta T4$ from the bedtime to a breakfast on the next day. In such a case, the times T1 to T4, at which the group excretion care is to be started respectively in the time periods $\Delta T1$ to $\Delta T4$ in the frequency distribution that has been generated in the generation process M12, are each set to the ending point of a time period in which the total number of times of defecation is the largest (at which the frequency is the highest) in the corresponding one of the time periods $\Delta T1$ to $\Delta T4$. Note that a method for specifying the times T1 to T4 at which the group excretion care is started is not limited to the method described above.

Alternatively, the processor 11 of the excretion care assistance device 1 may specify, in the second specification process M13, the times T1 to Tj at which the group excretion care is started, by inputting, into a time-point specification model, the frequency distribution that has been generated in the generation process M12. The time-point specification model has been subjected to machine learning using training data in which the frequency distribution indicative of the total number of times of defecation in each of the plurality of time periods is an explanatory variable, and the time periods at which the group excretion care is started are objective variables. To the machine learning for generating the time-point specification model, a known machine learning algorithm can be applied. Note that the time-point specification model may be stored in either one of the primary memory 12 and the secondary memory 13 of the excretion care assistance device 1 or alternatively may be stored in a device other than the excretion care assistance device 1.

The notification process M14 is a process for notifying the caregiver Ub of the times at which the group excretion care is to be started and which have been specified in the second specification process M13. In the notification process M14, the processor 11 of the excretion care assistance device 1 transmits, to the notification terminal 3, information including the times T1 to Tj at which the group excretion care is to be started and which have been specified in the second specification process M13 (first notification information). For example, this information further includes information indicative of a histogram prepared from the frequency distribution that has been generated in the generation process M12, as well as the above-described times T1 to Tj at which the group excretion care is started. Note that the information included in the first notification information is not limited and can include all the information related to the processes described above.

The notification terminal 3 that has received the first notification information displays, on the display the notification terminal 3 contains therein, a display screen for displaying various pieces of information included in the first notification information, to the caregiver Ub. A specific example of the display screen will be described later with reference to another drawing.

Note that the above-described processes in the excretion care assistance method M1 are carried out for each of the n care-receiver groups. That is, the time at which the group excretion care is to be started is specified for each of the n care-receiver groups.

Although the present embodiment assumes a case where the care-receivers Ua always wear the sensor terminals 2, the present invention is not limited to this case. For example, the care-receivers Ua wear the sensor terminals 2 only for a predetermined period (for example, one month), and during the predetermined period, the above-described processes in the excretion care assistance method M1 are carried out. After the sensor terminals 2 have been taken off, a user (for example, the caregiver Ub) may input the defecation times of the care-receivers Ua into the excretion care assistance device 1 so as to cause the processor 11 of the excretion care assistance device 1 to carry out the generation process M12, the second specification process M13, and the notification process M14.

Display Example

Figure 4:
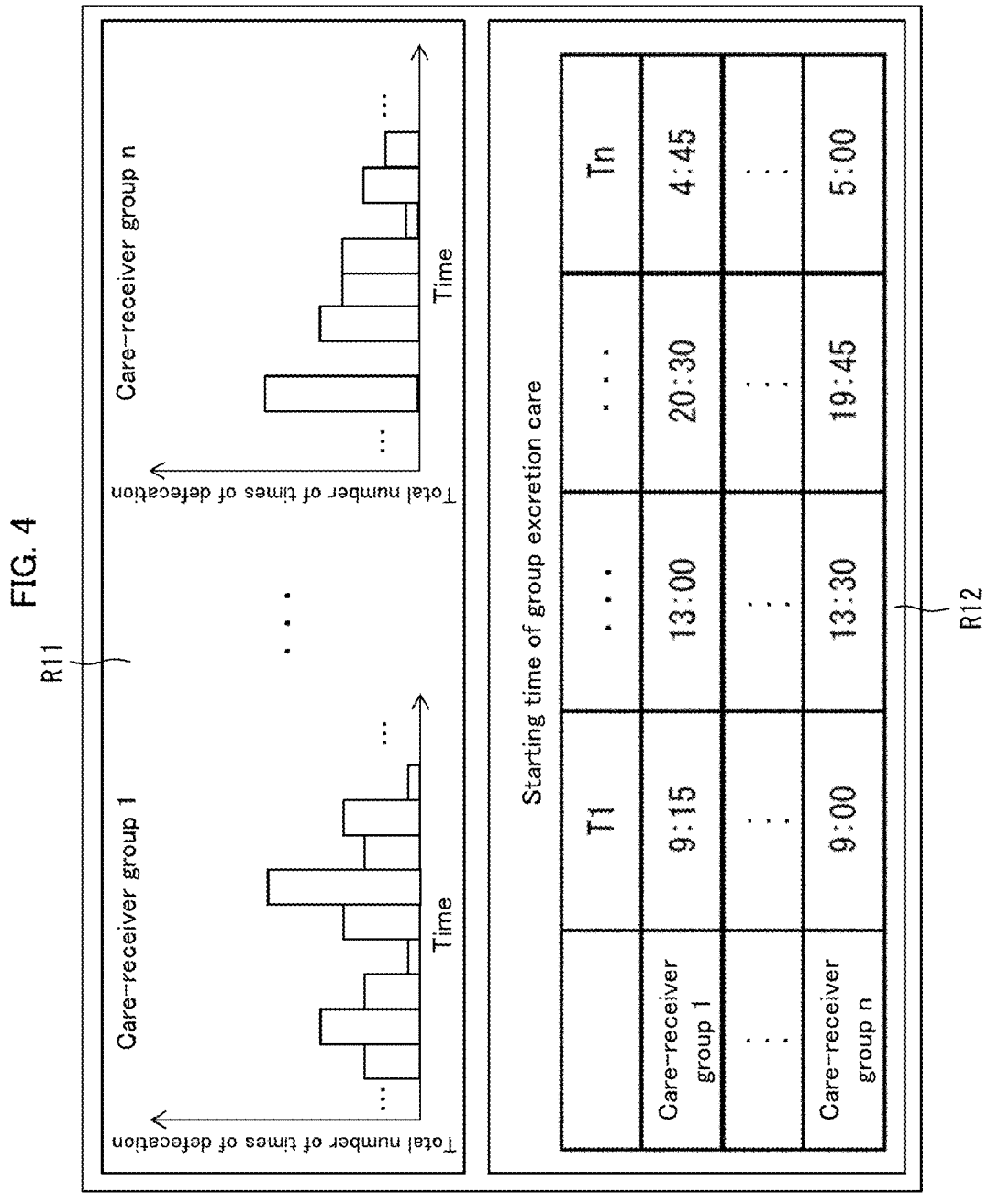
FIG. 4 is a view illustrating one example of a display screen displayed on a notification terminal, in the excretion care assistance method shown in FIG. 3.

With reference to FIG. 4, a display example will be described in which, to notify the caregiver Ub of the times T1 to Tj at which the group excretion care is to be started, the display screen is displayed on the display contained in the notification terminal 3. FIG. 4 is a view illustrating one display example of the display screen displayed by the notification terminal 3, in the excretion care assistance method M1.

As illustrated in FIG. 4, the display screen may display an area R11 and an area R12. The area R11 displays histograms each indicative of the total number of times of defecation in each of the plurality of time periods, in each of the n care-receiver groups. The area R12 displays a list of the times T1 to Tj at which the group excretion care is started, in each of the n care-receiver groups.

(Effect of Excretion Care Assistance System)

As described above, the excretion care assistance system S carries out the excretion care assistance method M1 so as to notify the caregiver Ub of the times at which the group excretion care is to be started and which take into consideration the defecation times of the care-receivers Ua.

Further, in a case where the excretion care assistance method M1 is repeatedly carried out, it is possible to easily adapt to change of the defecation times caused by, for example, physical conditions of the care-receivers Ua. This makes it possible for the caregiver Ub to provide excretion care after more care-receivers Ua have defecated. Thus, it is possible to reduce the number of times of the misses in the group excretion care, waste of diapers, and the number of times of the individual excretion care.

(Additional Function)

The excretion care assistance system S in accordance with the present embodiment may further include a function of estimating and notifying the number of the caregivers Ub needed for the excretion care.

Figure 5:
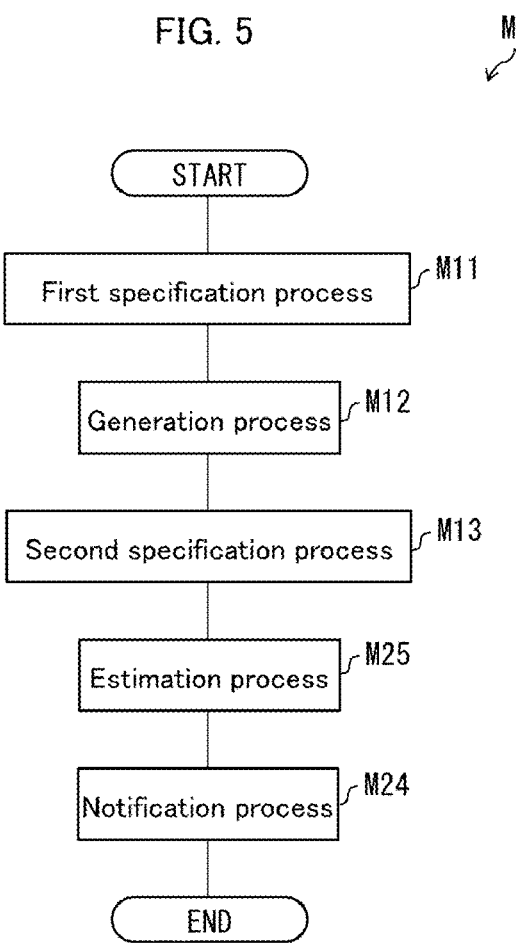
FIG. 5 is a flowchart showing a flow of an excretion care assistance method carried out in an excretion care assistance system in accordance with Embodiment 2 of the present invention.

With reference to FIG. 5, an excretion care assistance method that the excretion care assistance system S carries out in order to exert the above function (hereinafter, referred to as "excretion care assistance method M2") will be described. FIG. 5 is a flowchart illustrating a flow of the excretion care assistance method M2. For convenience of description, members which are identical in function to the members described above are given respective identical reference signs, and descriptions of those members will not be repeated.

As illustrated in FIG. 5, the excretion care assistance method M2 includes a first specification process M11, a generation process M12, a second specification process M13, and an estimation process M25, and a notification process M24. These processes are carried out periodically (for example, every month).

The estimation process M25 is a process for estimating the number of the caregivers Ub needed for the excretion care. In the estimation process M25, the processor 11 of the excretion care assistance device 1 estimates the number of the caregivers Ub needed for the excretion care for the care-receiver group i, in accordance with the frequency distribution that has been generated in the generation process M12. Here, the number of the caregivers Ub needed for the excretion care for the care-receiver group i may be estimated for each of a plurality of time periods $\Delta t1$ to $\Delta tk$ (k is any natural number of not less than 2) into which one day is divided.

In a case where the number of the caregivers Ub needed for the excretion care is estimated for each of time periods $\Delta t1$ to $\Delta t24$ into which one day is divided at one-hour intervals, a frequency distribution is generated in which classes are the time periods $\Delta t1$ to $\Delta t24$ and frequencies are the numbers of times of defecation in the time periods corresponding to the time periods $\Delta t1$ to $\Delta t24$, in the frequency distribution that has been generated in the generation process M12. The number of the caregivers Ub needed is estimated in accordance with the frequency in each of the time periods $\Delta t1$ to $\Delta t24$ in the frequency distribution generated. The correspondence between the frequency and the number of the caregivers Ub needed can be set as appropriate. For example, it is possible that the number of times of excretion care to be provided by caregiver Ub is preset, and on the basis of the preset number, the number of the caregivers Ub needed for the number of times of defecation (frequency) is estimated. In such a case, the number of times of excretion care to be provided by a single caregiver Ub is preferably inputted into the excretion care assistance device 1 in advance and, for example, may be inputted by a user (for example, a facility manager, the caregiver Ub, or the like) via the notification terminal 3.

Note that a method for estimating the number of the caregivers Ub needed for the excretion care for the care-receiver group i is not limited to the above-described method. Other examples of the method include a method as follows: among the time periods $\Delta t1$ to $\Delta t24$, in each time period including the time at which the group excretion care is to be started and which has been specified in the second specification process M13, the number of the caregivers Ub needed for the group excretion care for the care-receiver group i is estimated as the number of the caregivers Ub needed for the excretion care in the time period, and, in the other time periods, the needed number of the caregivers Ub that corresponds to the total number of times of defecation in each of the other time periods is estimated on the basis of the number of excretion care that a single caregiver Ub tackles.

Alternatively, the processor 11 of the excretion care assistance device 1 may estimate, in the estimation process M25, the number of the caregivers Ub needed for excretion care in each of the time periods Δt1 to Δtk, by inputting, into a caregiver-number estimation model, the frequency distribution that has been generated in the generation process M12. The caregiver-number estimation model has been subjected to machine learning using training data in which the frequency distribution indicative of the total number of times of defecation in each of the plurality of time periods is an explanatory variable and the number of caregivers needed for excretion care is an objective variable. To the machine learning for generating the caregiver-number estimation model, a known machine learning algorithm can be applied. Note that the caregiver-number estimation model may be stored in either one of the primary memory 12 and the secondary memory 13 of the excretion care assistance device 1 or alternatively may be stored in a device other than the excretion care assistance device 1.

The notification process M24 is a process for notifying a user (for example, a facility manager) of the number of the caregivers Ub needed for the excretion care, the number having been estimated in the estimation process M25. In the notification process M24, the processor 11 of the excretion care assistance device 1 transmits, to the notification terminal 3, information including, for example, a result of estimation of the number of the caregivers Ub needed for the excretion care in each of the time periods Δt1 to Δtk (second notification information). This information can include, as well as the above-described estimation result of the number of the caregivers Ub needed for excretion care, all the information related to the above-described processes, such as information indicative of the histogram prepared from the frequency distribution that has been generated in the generation process M12.

The notification terminal 3 that has received the second notification information displays, on the display that the notification terminal 3 contains therein, a display screen for displaying various pieces of information included in the second notification information, to the caregiver Ub. A specific example of the display screen will be described later with reference to another drawing.

Note that the above-described processes in the excretion care assistance method M2 are carried out for each of the n care-receiver groups. In this case, in each of the time periods Δt1 to Δtk, the number of the caregivers Ub needed for the excretion care is a total of the numbers of the caregivers Ub needed for excretion care, the numbers having been estimated for the n care-receiver groups.

Further, although the present additional function assumes a case where the care-receivers Ua always wear the sensor terminals 2, the present invention is not limited to this case. For example, the care-receivers Ua wear the sensor terminals 2 only for a predetermined period (for example, one year), and during the predetermined period, the above-described processes in the excretion care assistance method M2 are carried out. After the sensor terminals 2 have been taken off, a user (for example, the caregiver Ub) may input the defecation times of the care-receivers Ua into the excretion care assistance device 1 so as to cause the processor 11 of the excretion care assistance device 1 to carry out the generation process M12, the second specification process M13, the estimation process M25, and the notification process M24.

Display Example

Figure 6:
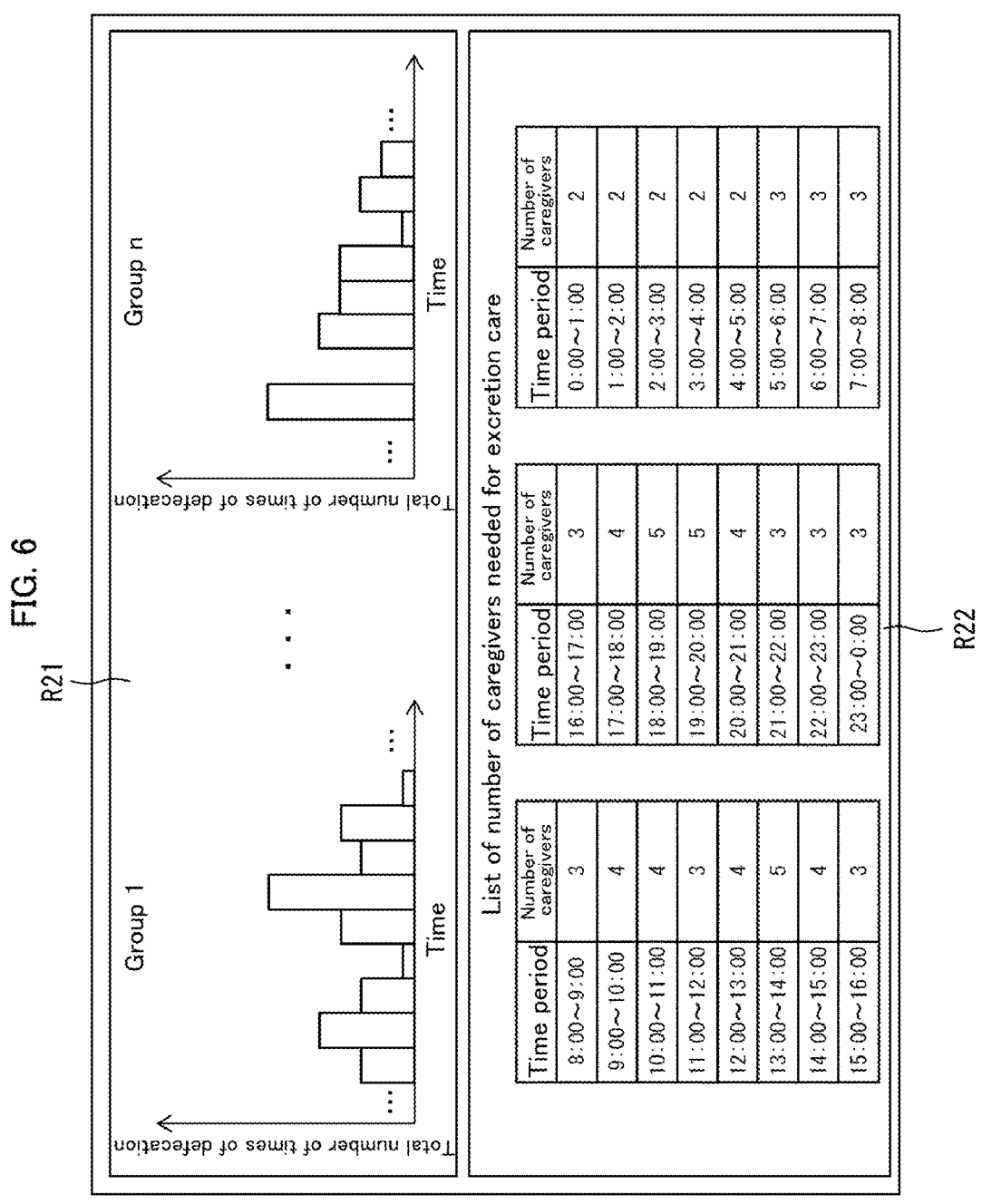
FIG. 6 is a view illustrating one example of a display screen displayed on a notification terminal, in the excretion care assistance method shown in FIG. 5.

With reference to FIG. 6, a display example of the display screen will be described in which, to notify the number of the caregivers Ub needed for the excretion care, the display screen is displayed on the display contained in the notification terminal 3. FIG. 6 is a view illustrating one display example of the display screen displayed by the notification terminal 3, in the excretion care assistance method M2.

As illustrated in FIG. 6, the display screen may display an area R21 and an area R22. The area R21 displays histograms each indicative of the total number of times of defecation in each of a plurality of time periods. The area R22 displays a list of the number of the caregivers Ub needed for the excretion care in each of a plurality of time periods Δt1 to Δtk into which one day is divided (is divided at one-hour intervals in FIG. 6).

(Effect of Additional Function)

The excretion care assistance system S in accordance with the variation as described above carries out the excretion care assistance method M2 so as to estimate and notify the number of the caregivers Ub needed for excretion care. This enables a user (for example, a facility manager) to prepare a shift schedule for the caregivers Ub which takes into consideration the number of the caregivers Ub needed for excretion care, thereby contributing to efficiently completing excretion care and other operations.

Additional Remarks

The present invention is not limited to the embodiments, but can be altered by a skilled person in the art within the scope of the claims. The present invention also encompasses, in its technical scope, any embodiment derived by combining technical means disclosed in differing embodiments.

Recap

An excretion care assistance device in accordance with Aspect 1 of the present embodiment includes at least one processor configured to carry out: a first specification process of specifying defecation times of care-receivers included in at least one care-receiver group on the basis of output signals from sensor terminals which are worn by the care-receivers and which include excretion sensors; and a second specification process of specifying a time at which group excretion care is to be started for the at least one care-receiver group, in accordance with a frequency distribution indicative of a total number of times of defecation in each of a plurality of time periods, the frequency distribution being determined from the defecation times that have been specified in the first specification process.

According to the above configuration, it is possible to specify the time at which the group excretion care is started, in view of the defecation times of the care-receivers. This makes it possible to reduce the number of times of the misses in the group excretion care.

An excretion care assistance device in accordance with Aspect 2 of the present embodiment is configured, in Aspect 1, such that, in the second specification process, the at least one processor specifies, as the time at which the group excretion care is to be started for the at least one care-receiver group, an ending point of a time period in which the total number of times of defecation is the largest, among the plurality of time periods.

According to the above configuration, as in the case of Aspect 1, it is possible to reduce the number of times of the miss in the group excretion care.

An excretion care assistance device in accordance with Aspect 3 of the present embodiment is configured, in Aspect 1 or 2, such that the at least one care-receiver group includes a plurality of care-receiver groups, and the at least one processor specifies a time at which group excretion care is to be started, for each of the plurality of care-receiver groups, by carrying out the first specification process, a generation process, and the second specification process for each of the plurality of care-receiver groups.

According to the above configuration, it is possible to specify the time at which the group excretion care is started, for each of the plurality of care-receiver groups. This makes it possible to provide efficient group excretion care irrespective of, for example, a scale of the facility.

An excretion care assistance device in accordance with Aspect 4 of the present embodiment is configured, in Aspects 1 to 3, to further carry out an estimation process of estimating, in accordance with the frequency distribution, the number of caregivers needed for excretion care for the at least one care-receiver group.

According to the above configuration, it is possible to estimate the number of caregivers needed for excretion care as well as to specify the time at which the group excretion care is started. This makes it possible to establish a work system in which the caregivers who provide excretion care are sufficiently ensured. This makes it possible to efficiently provide both excretion care and other operations.

An excretion care assistance method in accordance with Aspect 5 of the present embodiment includes: carrying out a first specification process with at least one processor specifying defecation times of care-receivers included in at least one care-receiver group on the basis of output signals from sensor terminals which are worn by the care-receivers and which include excretion sensors; and carrying out a second specification process of specifying a time at which group excretion care is to be started for the at least one care-receiver group, in accordance with a frequency distribution indicative of a total number of times of defecation in each of a plurality of time periods, the frequency distribution being determined from the defecation times that have been specified in the first specification process.

The above configuration exerts an effect similar to that of Aspect 1.

The invention claimed is:

1. An excretion care assistance device comprising at least one processor configured to carry out:

a first specification process of specifying defecation times of care-receivers included in at least one care-receiver group on the basis of output signals from sensor terminals which are worn by the care-receivers and which include excretion sensors; and a second specification process of specifying a time at which group excretion care is to be started for the at least one care-receiver group, in accordance with a frequency distribution indicative of a total number of times of defecation in each of a plurality of time periods, the frequency distribution being determined from the defecation times that have been specified in the first specification process.

2. The excretion care assistance device according to claim 1, wherein, in the second specification process, the at least one processor specifies, as the time at which the group excretion care is to be started for the at least one care-receiver group, an ending point of a time period in which the total number of times of defecation is the largest, among the plurality of time periods.

3. The excretion care assistance device according to claim 1, wherein:

the at least one care-receiver group comprises a plurality of care-receiver groups; and the at least one processor specifies a time at which group excretion care is to be started, for each of the plurality of care-receiver groups, by carrying out the first specification process and the second specification process for each of the plurality of care-receiver groups.

4. The excretion care assistance device according to claim 1, configured to further carry out an estimation process of estimating, in accordance with the frequency distribution, the number of caregivers needed for excretion care for the at least one care-receiver group.

5. An excretion care assistance method comprising:

carrying out a first specification process with at least one processor specifying defecation times of care-receivers included in at least one care-receiver group on the basis of output signals from sensor terminals which are worn by the care-receivers and which include excretion sensors; and carrying out a second specification process of specifying a time at which group excretion care is to be started for the at least one care-receiver group, in accordance with a frequency distribution indicative of a total number of times of defecation in each of a plurality of time periods, the frequency distribution being determined from the defecation times that have been specified in the first specification process.

6. The excretion care assistance device according to claim 2, wherein, in the second specification process, the at least one processor is configured to specify the ending point of a time period by inputting the frequency distribution into a time-point specification model that has been subjected to machine learning using training data in which the frequency distribution is an explanatory variable, and the plurality of time periods are objective variables.

7. The excretion care assistance device according to claim 4, wherein, in the estimation process, the number of caregivers is estimated based on the frequency distribution inputted into a caregiver-number estimation model that has been subjected to machine learning using training data in which the frequency distribution is an explanatory variable and the number of caregivers is an objective variable.

* * * * *